US010610177B2

(12) United States Patent
Biermann et al.

(10) Patent No.: US 10,610,177 B2
(45) Date of Patent: Apr. 7, 2020

(54) METHOD FOR IMAGING BY MEANS OF AN X-RAY DEVICE AND X-RAY DEVICE

(71) Applicant: SIEMENS AKTIENGESELLSCHAFT, Munich (DE)

(72) Inventors: Volker Biermann, Forchheim (DE); Frank Dennerlein, Forchheim (DE); Michael Fuhrmann, Herzogenaurach (DE); Rainer Graumann, Hoechstadt (DE); Anna Jerebko, Hausen (DE); Thomas Mertelmeier, Erlangen (DE); Ralf Nanke, Neunkirchen am Brand (DE); Thomas Schmitt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 383 days.

(21) Appl. No.: 14/909,259

(22) PCT Filed: Jun. 13, 2014

(86) PCT No.: PCT/EP2014/062310
§ 371 (c)(1),
(2) Date: Feb. 1, 2016

(87) PCT Pub. No.: WO2015/014525
PCT Pub. Date: Feb. 5, 2015

(65) Prior Publication Data
US 2016/0183892 A1   Jun. 30, 2016

(30) Foreign Application Priority Data
Jul. 31, 2013   (DE) .................. 10 2013 215 043

(51) Int. Cl.
A61B 6/00   (2006.01)

(52) U.S. Cl.
CPC .......... *A61B 6/4452* (2013.01); *A61B 6/4085* (2013.01); *A61B 6/4458* (2013.01); *A61B 6/4464* (2013.01); *A61B 6/5241* (2013.01)

(58) Field of Classification Search
CPC ... A61B 6/4085; A61B 6/4452; A61B 6/4458; A61B 6/4464; A61B 6/5241
See application file for complete search history.

(56) References Cited

U.S. PATENT DOCUMENTS 3,784,837 A * 1/1974 Holmstrom .......... A61B 6/4441
378/189
6,200,024 B1 * 3/2001 Negrelli .............. A61B 6/4233
378/196

(Continued)

FOREIGN PATENT DOCUMENTS

CN   1647768 A   8/2005
CN   102429672 A   5/2012

(Continued)

*Primary Examiner* — David J Makiya
*Assistant Examiner* — Soorena Kefayati
(74) *Attorney, Agent, or Firm* — Laurence Greenberg; Werner Stemer; Ralph Locher

(57) ABSTRACT

A first x-ray image is acquired at a predetermined position of a focal point and with a first orientation of an x-ray tube of an x-ray device. Subsequently, the x-ray tube is adjusted by rotating about a predetermined angle and by positioning, wherein the focal point is situated in the predetermined position prior to the adjustment and after the adjustment. After the adjustment, the x-ray tube is situated in a second orientation. Subsequently, a second x-ray image is acquired at the predetermined position and with the second orientation. A combined x-ray image from at least the first and second x-ray image is produced.

7 Claims, 5 Drawing Sheets

(56) References Cited

U.S. PATENT DOCUMENTS

| | | | | |
|---|---|---|---|---|
| 6,325,537 B1* | 12/2001 | Watanabe | A61B 6/4233 378/196 |
| 6,435,715 B1* | 8/2002 | Betz | A61B 6/4458 378/197 |
| 6,510,194 B1* | 1/2003 | Arakawa | A61B 6/032 378/19 |
| 6,872,000 B2* | 3/2005 | Atzinger | A61B 6/4233 378/197 |
| 7,016,458 B2* | 3/2006 | Francke | A61B 6/032 378/19 |
| 7,018,097 B2* | 3/2006 | Schmitt | A61B 6/4441 378/197 |
| 7,020,234 B2 | 3/2006 | Bruder et al. | |
| 7,401,977 B2* | 7/2008 | Graumann | A61B 6/4441 378/197 |
| 7,566,171 B2* | 7/2009 | Fuhrmann | A61B 6/4441 378/197 |
| 8,213,565 B2* | 7/2012 | Boese | A61B 6/032 378/20 |
| 8,693,638 B2* | 4/2014 | Dafni | A61B 6/032 378/124 |
| 9,107,633 B2 | 8/2015 | Muller | |
| 9,214,311 B2* | 12/2015 | Funk | A61B 6/4064 |
| 9,460,823 B2* | 10/2016 | Song | H05K 7/2039 |
| 9,492,125 B2* | 11/2016 | Deutschmann | A61B 6/03 |
| 2002/0118793 A1* | 8/2002 | Horbaschek | A61B 6/4233 378/197 |
| 2004/0240609 A1* | 12/2004 | Spahn | A61B 6/488 378/63 |
| 2007/0086570 A1* | 4/2007 | Spahn | A61B 6/102 378/117 |
| 2008/0089468 A1* | 4/2008 | Heigl | A61B 6/032 378/20 |
| 2008/0152088 A1* | 6/2008 | Wang | A61B 6/02 378/98.12 |
| 2009/0074148 A1* | 3/2009 | Echner | G21K 1/04 378/152 |
| 2009/0080598 A1* | 3/2009 | Tashman | A61B 5/1038 378/11 |
| 2010/0067762 A1* | 3/2010 | Glocker | A61B 6/5241 382/131 |
| 2010/0172472 A1* | 7/2010 | Ermes | A61B 6/5241 378/62 |
| 2011/0051887 A1* | 3/2011 | Kunze | A61B 6/032 378/11 |
| 2011/0051895 A1* | 3/2011 | Vogtmeier | A61B 6/032 378/92 |
| 2011/0069812 A1* | 3/2011 | Takahashi | A61B 6/025 378/21 |
| 2011/0069818 A1* | 3/2011 | Muller | A61B 6/4464 378/197 |
| 2011/0237941 A1* | 9/2011 | Shahar | A61B 6/032 600/427 |
| 2012/0027169 A1* | 2/2012 | Nakayama | A61B 6/022 378/41 |
| 2012/0029694 A1* | 2/2012 | Muller | A61B 6/0407 700/248 |
| 2012/0059239 A1* | 3/2012 | Yamaguchi | G06T 7/20 600/407 |
| 2013/0216023 A1* | 8/2013 | Graumann | A61B 6/5241 378/62 |
| 2013/0315372 A1* | 11/2013 | Behiels | A61B 6/06 378/62 |
| 2014/0140481 A1 | 5/2014 | Yamaguchi | |
| 2015/0117603 A1* | 4/2015 | Keeve | A61B 6/0407 378/62 |
| 2015/0265237 A1* | 9/2015 | Keeve | A61B 6/032 378/41 |
| 2015/0297158 A1* | 10/2015 | Bothorel | A61B 6/06 378/20 |
| 2015/0297159 A1* | 10/2015 | Melman | G21K 1/04 378/62 |
| 2016/0302746 A1* | 10/2016 | Erhard | A61B 6/4452 |

FOREIGN PATENT DOCUMENTS

| | | |
|---|---|---|
| DE | 10215982 A1 | 11/2003 |
| DE | 102009047867 A1 | 4/2011 |
| DE | 102010038800 A1 | 2/2012 |
| DE | 102011089178 A1 | 6/2013 |

\* cited by examiner

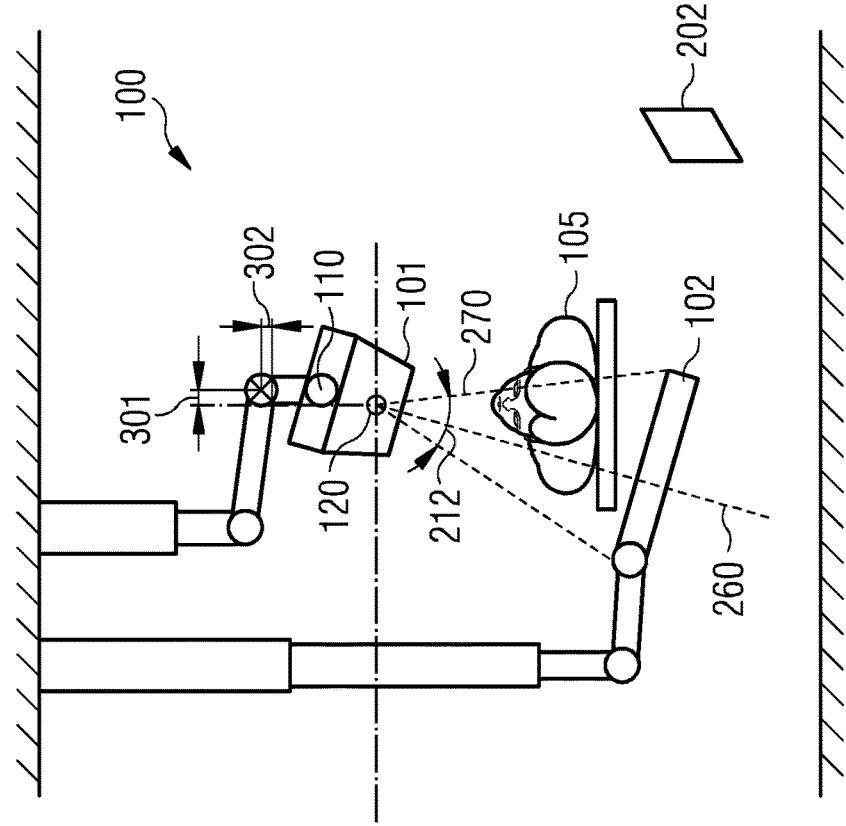
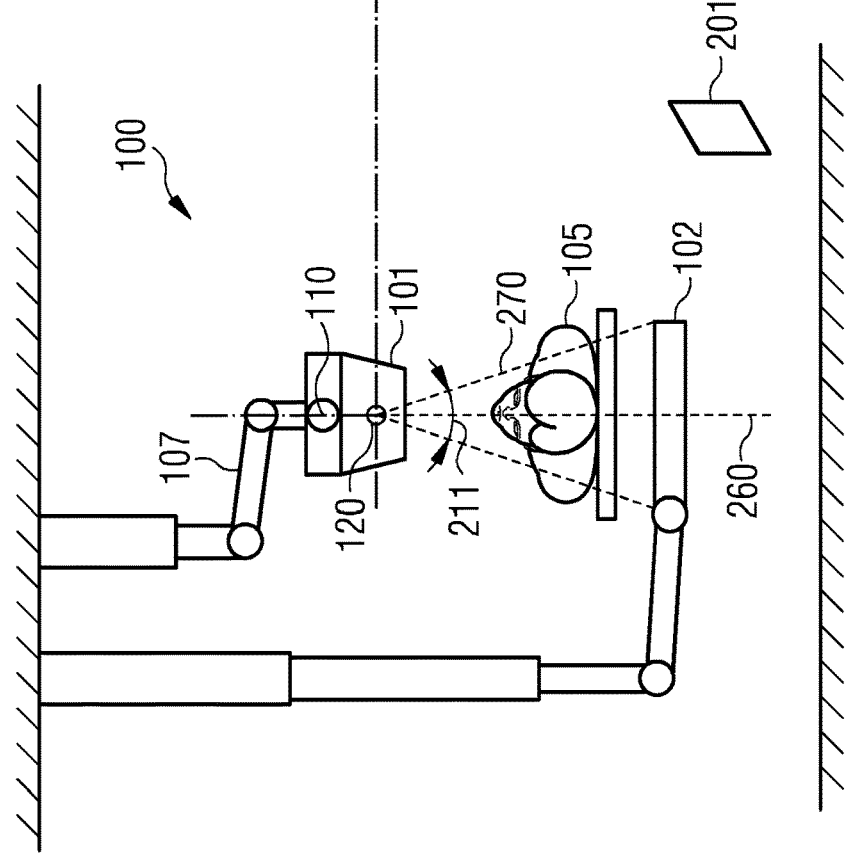

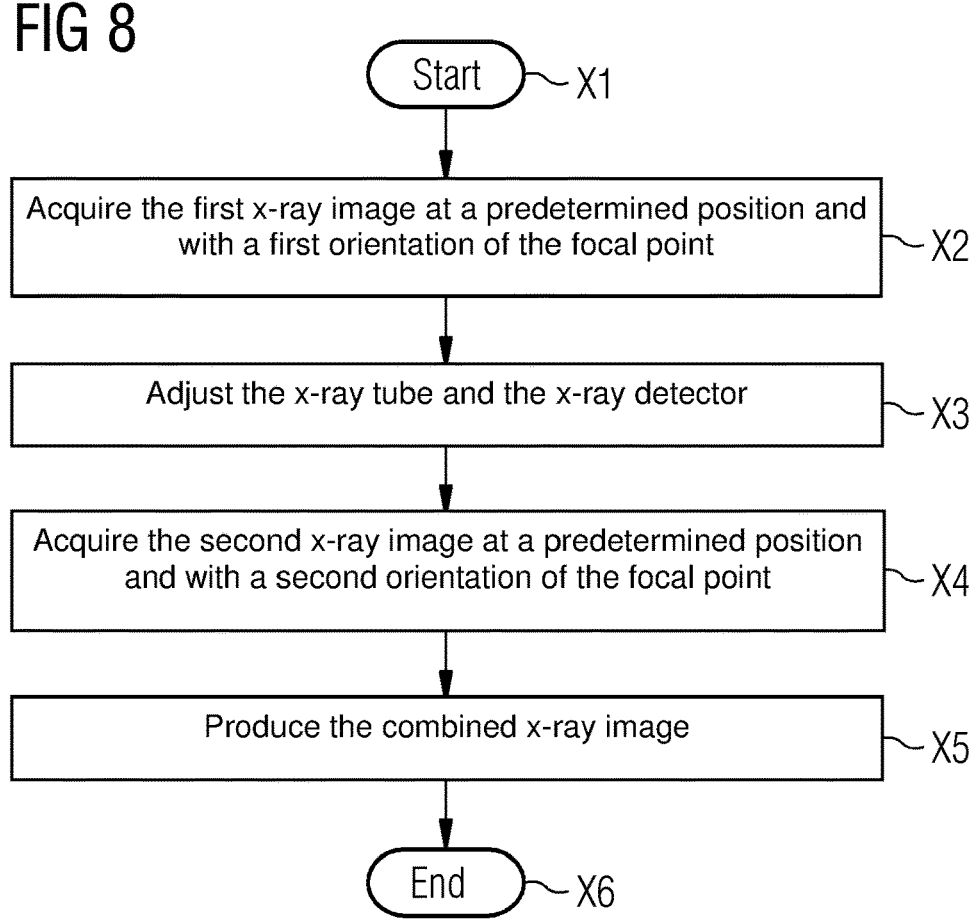
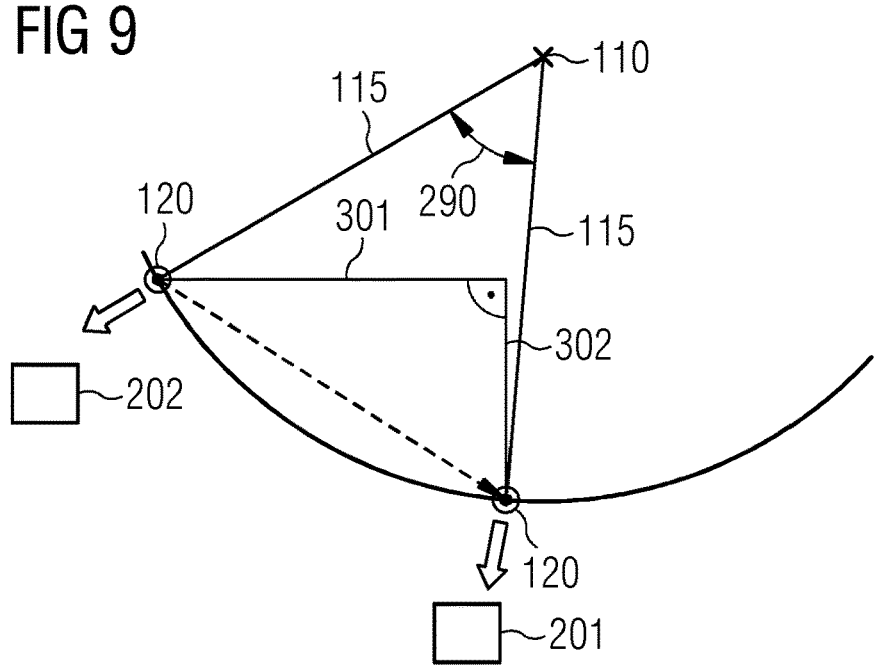

METHOD FOR IMAGING BY MEANS OF AN X-RAY DEVICE AND X-RAY DEVICE

BACKGROUND OF THE INVENTION

Field of the Invention

The invention relates to a method for imaging by means of an x-ray device and an x-ray device. In particular, the invention relates to various techniques, in which a first and a second x-ray image are acquired at a predetermined position of a focal point and with different orientations of an x-ray tube of the x-ray device and a combined x-ray image is produced therefrom.

Techniques for imaging by means of an x-ray device are known. Here, x-rays, i.e. electromagnetic radiation in the wavelength range from approximately $10^{-3}$ nm to approximately 10 nm, are typically produced by means of an x-ray tube. The x-rays can be measured by means of an x-ray detector of the x-ray device after being transmitted through an object to be examined and they can be used for imaging.

The x-ray device often has a so-called cone beam geometry of the x-rays. In such a case, a beam path of the x-rays is conical, i.e. it broadens from an initial point of the x-ray radiation (focal point) at the x-ray tube with increasing distance from the focal point. This means that the cross-sectional area of the beam path of the x-rays is larger (smaller) in the case of a larger (smaller) distance from the focal point. A central ray of the beam path is typically situated at the center of the cross-sectional area. By way of example, the central ray can define an orientation of the focal point.

Typically, the finite cross-sectional area of the beam path of the x-rays limits a region of the examination object that can be imaged in a single exposure pass. If an area of the examination object to be examined is greater than the imageable region, it may be necessary to successively acquire a plurality of x-ray images within the scope of a plurality of exposure passes and to subsequently produce a combined x-ray image from the plurality of acquired x-ray images.

To this end, there can be an orientation of the x-ray tube or of the focal point between the acquisition of two x-ray images in accordance with various techniques already known. The angle of the emission of the x-rays can be modified by the orientation of the x-ray tube. The central ray is aligned.

However, such techniques that are already known have various restrictions. In conventional x-ray devices, a focal point is typically at a distance from a point of rotation of the x-ray tube, about which a rotation is carried out when orienting the x-ray tube. Therefore, there can be so-called parallax errors when producing the combined x-ray image from the plurality of acquired x-ray images. Parallax errors typically occur due to the cone beam geometry of the x-ray device: the plurality of acquired x-ray images do not fit together, or only fit together to a restricted extent, in terms of geometry since, for example, an image scale and/or a perspective can change from x-ray image to x-ray image. Usability of such combined x-ray images with significant parallax errors, for example within the scope of the subsequent medical diagnosis, may not be given, or only given to a restricted extent.

In order to solve these restrictions, techniques in which operating staff undertake a manual alignment of the x-ray tube for each acquisition of an x-ray image are known. Such techniques can be comparatively time intensive, error afflicted and therefore cost intensive.

Furthermore, techniques which remove, or at least reduce, the parallax errors by means of image processing algorithms are known. However, the use of such image processing algorithms may be comparatively complicated. For example, it may be necessary to provide dedicated computational capacity for carrying out the image processing algorithms.

BRIEF SUMMARY OF THE INVENTION

Hence, there is a need for improved techniques for imaging by means of an x-ray device, in which a combined x-ray image is produced from a plurality of x-ray images. In particular, there is a need for such techniques which enable a particularly simple production of the combined x-ray image. There is a need for techniques, in which the combined x-ray image has no, or only small, parallax errors.

This object is achieved by the features of the independent claims. The dependent claims define embodiments.

In accordance with one aspect, the invention relates to a method for imaging by means of an x-ray device, which comprises an x-ray tube and an x-ray detector. The position of a focal point of the x-ray tube is adjustable by positioning the x-ray tube. An orientation of the x-ray tube is adjustable by rotating the x-ray tube about a point of rotation. The point of rotation is spaced apart from the focal point by a distance. The method comprises the acquisition of a first x-ray image at a predetermined position of the focal point and with a first orientation of the x-ray tube. Furthermore, the method comprises the adjustment of the x-ray tube by a rotation about a predetermined angle and by positioning, wherein the focal point is at the predetermined position prior to the adjustment and after the adjustment and wherein the x-ray tube has a second orientation after the adjustment. Furthermore, the method comprises the acquisition of a second x-ray image at the predetermined position of the focal point and with the second orientation of the x-ray tube. The method furthermore comprises the production of a combined x-ray image from at least the first x-ray image and the second x-ray image.

By way of example, the position and/or the orientation can be defined in relation to the examination object to be imaged. It would also be possible for the position and/or the orientation to be defined in relation to a machine coordinate system of the x-ray device. It would also be possible for the position and/or the orientation to be defined in relation to a different reference coordinate system which, for example, emerges from different technical and/or medical boundary conditions. The orientation of the x-ray tube can be directly indicative for the orientation of the focal point. The orientation and the position of the x-ray tube or of the focal point together can also be referred to as a so-called pose. The pose can denote the arrangement and alignment of the x-ray tubes or of the focal point relevant to the imaging.

It is possible that the orientation of the x-ray tube is directly indicative for an orientation of the focal point, in particular in relation to an emission direction of the x-rays or in relation to an alignment of the central ray of the x-rays. Accordingly, the focal point as an initial point of the x-rays can denote the area from which the x-rays emanate. In relation to the focal point, a distinction can typically be made between a thermal focal spot, i.e. that area of an anode of the x-ray tube which is hit by an electron beam. The decelerating of electrons of the electron beam in turn can generate the x-ray radiation. Furthermore, it is possible to differentiate in respect of an electronic focal spot as the intersection of the electron beam with a surface of the anode and an optical focal spot, which denotes the focal point effective for the imaging by means of the x-ray device. Below, reference is made, in particular, to the optically effective focal point.

When the point of rotation is spaced apart from the focal point by a distance, an orientation of the x-ray tube by rotation about the point of rotation typically brings about a change in the position of the focal point at the same time. However, what can be achieved by adjusting the x-ray tube is that this change in the position of the focal point is compensated for by appropriate positioning. What this can achieve is that all that is changed when acquiring the first and the second x-ray image is the orientation of the x-ray tube or of the focal point, but the position of the focal point or of the x-ray tube remains substantially unchanged. Rotating and positioning can be carried out in any order and/or at least partly in parallel.

By way of example, the position of the focal point or the x-ray tube can be equal within a certain positioning accuracy of the x-ray device when acquiring the first and second x-ray image, i.e. prior to and after the adjustment. By way of example, such a positioning accuracy of the x-ray device can be given inherently by technical limitations, for example by using stepper motors, etc.

Such previously described techniques can also be referred to as a virtual rotation about the focal point of the x-ray tube. Although orienting by way of a rotation about the point of rotation and the corresponding positioning of the x-ray tube are carried out mechanically, the combination of rotating and positioning, i.e. the adjustment, can be described as a virtual rotation about the focal point.

What is rendered possible by means of such techniques described above is that the combined x-ray image has no, or only small, parallax errors. Moreover, it may be possible to reduce the period of time to the production of the combined x-ray image (measurement duration). This may render it possible to reduce costs.

It is possible that the x-ray detector is adjustable in a manner decoupled from the x-ray tube. The adjustment can furthermore comprise the adjustment of the x-ray detector by rotating and positioning the x-ray detector. Prior to the adjustment and after the adjustment, a detector plane of the x-ray detector can lie perpendicular to the central ray of x-rays in each case. Alternatively or additionally, a film/focus distance between the focal point and the detector plane can be the same in each case prior to the adjustment and after the adjustment. Alternatively or additionally, the central ray can be placed substantially centrally on the x-ray detector prior to the adjustment and after the adjustment.

By way of example, the central ray can denote an axis of symmetry of the cone beam geometry of the x-ray device. The central ray can therefore be emitted from the focal point of the x-ray tube and respectively lie at the center point of the cross-sectional area of the x-rays. As explained above, the central ray can define the orientation of the focal point or of the x-ray tube.

Thus, it is possible to adjust, firstly, the x-ray tube and, secondly, the x-ray detector within the scope of the adjustment. An order of the adjustment, in particular of the positioning and the orienting, is often irrelevant here. However, it may be essential for the adjustment to be complete before the second x-ray image is acquired. The position and the orientation of the x-ray detector can be defined in a manner corresponding or analogous to the definition of position and orientation of the x-ray tube.

A particularly comprehensive suppression or reduction of parallax errors can be achieved by adjusting the x-ray tube and the x-ray detector. What can be achieved by placing the central ray substantially centrally on the x-ray detector is that the corresponding x-ray image images a particularly large region of the examination object.

The film/focus distance can influence or set the imaging scale of the respective x-ray image. If the film/focus distance is selected to be the same when acquiring the first and second x-ray image, the imaging scale for the first and second x-ray image can be the same. This means that the corresponding parameters of the first and second x-ray image can be selected to be the same and a correspondingly simple production of the combined x-ray image is possible.

The same applies to adjusting the x-ray detector in such a way that the central ray respectively lies perpendicular to the detector plane of the x-ray detector. This is because tilting the detector plane away from this configuration can cause distortions to be present in the corresponding x-ray image, which make the production of the combined x-ray image more difficult, or prevent the latter.

The positioning of the focal point can comprise a longitudinal component and/or a transverse component. The longitudinal component and/or the transverse component can be determined on the basis of the distance between the point of rotation and the focal point and on the basis of the predetermined angle. By way of example, the longitudinal component and the transverse component can denote a positioning of the focal point along and perpendicular to the central ray. It would also be possible for the longitudinal component and the transverse component to denote a positioning of the focal point in the horizontal and vertical direction or in the vertical direction and horizontal direction. It would also be possible for the longitudinal component and the transverse component to be denoted as components in the machine coordinate system or in the reference coordinate system. In general, motors with corresponding degrees of freedom can be provided for the positioning of the focal point or of the x-ray tube such that the positioning of the focal point occurs as a superposition of a displacement along the corresponding degrees of freedom of the provided motors. The distance between the point of rotation and the focal point can be known in advance, as it is typically determined by the construction and does not vary, or only varies a little, as a function of time and/or temperature. Together with knowledge about the predetermined angle, about which the rotation takes place within the scope of the orientation of the x-ray tube or of the focal point, it may then be possible to determine by means of geometric considerations how the positioning of the focal point is to take place such that the focal point lies at the same position prior to and after the adjustment. It would also be possible to take drifts of the focal point as a function of time and/or temperature into consideration.

The method can furthermore comprise encompassing an x-ray stop in a beam path of the x-rays in such a way that a first solid angle exposed when acquiring the first x-ray image and a second solid angle exposed when acquiring the second x-ray image have a predetermined overlap.

The x-ray stop can completely or largely absorb x-ray radiation. As a result, the beam path of the x-rays can be restricted or limited.

In this respect, it may be possible, for example, for the predetermined angle, about which the x-ray tube is rotated within the scope of orientation, to be smaller than an aperture angle of the beam path, i.e. smaller than the solid angle into which x-rays are emitted when acquiring the first and second x-ray image. In such a case, there can be a significant overlap of the exposed solid angles without arranging the x-ray stop. What can be achieved by arranging the x-ray stop is that a predetermined overlap is obtained between the first and second solid angle. By way of example, the predetermined overlap can be relatively small or equal to zero. As a result, it may be possible to achieve a reduction in the x-ray dose deposited in the examination object. A radiation exposure of the examination object, for example a patient under examination, can be reduced.

By way of example, it is possible that the combined x-ray image is produced by superposing the first x-ray image and the second x-ray image. This is because if e.g. parameters of the first and second x-ray image, such as pose, i.e. orientation and positioning, imaging scale, etc. are comparable, the production of the combined x-ray image can be carried out in a particularly simple manner by superposition. In particular, it may be possible to dispense with the application of further image processing algorithms on the first and second x-ray image within the scope of producing the combined x-ray image. It may also be possible to dispense with the production of a combined x-ray image requiring manual user inputs.

As a result of this, it may be possible to achieve a particularly quick production of the combined x-ray image. The production of the combined x-ray image can require comparatively little computational capacity.

By way of example, the method can furthermore comprise obtaining a solid angle region which is intended to be imaged by the combined x-ray image by means of a user interface. The method can furthermore comprise the calculation of the predetermined angle as a function of the obtained solid angle region.

As a result of this, it is possible to achieve a particularly simple implementation of the imaging by means of the x-ray device. In particular, a user can make do without having to consider the various geometric relationships of the x-ray device which influence the imaging. The corresponding parameters can be set automatically, or largely automatically, by means of the techniques described above.

In accordance with a further aspect, the invention relates to an x-ray device, which comprises an x-ray tube and an x-ray detector. A position of a focal point of the x-ray tube is adjustable by positioning the x-ray tube. An orientation of the x-ray tube is adjustable by rotating the x-ray tube about a point of rotation. The point of rotation is spaced apart from the focal point by a distance. The x-ray device furthermore comprises a control unit which is configured to carry out the following steps: acquiring a first x-ray image at a predetermined position of the focal point and with a first orientation of the x-ray tube; and adjusting the x-ray tube by a rotation about a predetermined angle and by positioning. Here, the focal point is at the predetermined position prior to the adjustment and after the adjustment. The x-ray tube has a second orientation after the adjustment. The control unit is furthermore configured to acquire a second x-ray image at the predetermined position of the focal point and with the second orientation of the x-ray tube. The x-ray device furthermore comprises a computer unit, which is configured to carry out the following step: producing a combined x-ray image from at least the first x-ray image and the second x-ray image.

The x-ray detector can be adjustable in a manner decoupled from the x-ray level, wherein the control unit is furthermore configured in such a way that the adjustment furthermore comprises the adjustment of the x-ray detector by rotating and positioning the x-ray detector. Prior to the adjustment and after the adjustment, a detector plane of the x-ray detector can lie perpendicular to the central ray of x-rays in each case, and/or a film/focus distance between the focal point and the detector plane can be the same in each case; and/or the central ray can be placed substantially centrally on the detector.

The positioning of the focal point can comprise a longitudinal component and/or a transverse component. The longitudinal component and/or the transverse component can be determined on the basis of the distance between the point of rotation and the focal point and on the basis of the predetermined angle.

The x-ray device can furthermore comprise an x-ray stop, wherein the control unit can be furthermore configured to carry out the following step: arranging the x-ray stop in a beam path of the x-rays in such a way that a first solid angle exposed when acquiring the first x-ray image and a second solid angle exposed when acquiring the second x-ray image have a predetermined overlap.

The x-ray device in accordance with the present aspect of the invention can furthermore be configured to carry out the method for imaging by means of an x-ray device in accordance with a further aspect of the present invention.

For such an x-ray device, it is possible to obtain effects which are comparable to the effects which can be achieved for the method for imaging by means of an x-ray device in accordance with a further aspect of the present invention.

The features presented above and features which are described below can be used not only in the correspondingly explicitly presented combinations, but also in other combinations or on their own, without departing from the field of the invention.

The properties, features and advantages of this invention described above, and the manner in which they are achieved, will become clearer and more easily understandable in conjunction with the following description of the exemplary embodiments, which are explained in more detail in conjunction with the drawings.

BRIEF DESCRIPTION OF THE SEVERAL VIEWS OF THE DRAWING

FIG. 3 shows the acquisition of a first x-ray image by means of the x-ray device from FIG. 2, wherein the focal point of the x-ray tube is in a first orientation.

FIG. 4 shows the acquisition of a second x-ray image by means of the x-ray device from FIG. 2, wherein the focal point of the x-ray tube is in a second orientation.

FIG. 8 is a flowchart of a method for imaging by means of an x-ray device in accordance with various embodiments of the present invention.

FIG. 9 illustrates geometric relationships between the focal point and the point of rotation in the first and second orientation.

DESCRIPTION OF THE INVENTION

Figure 1:
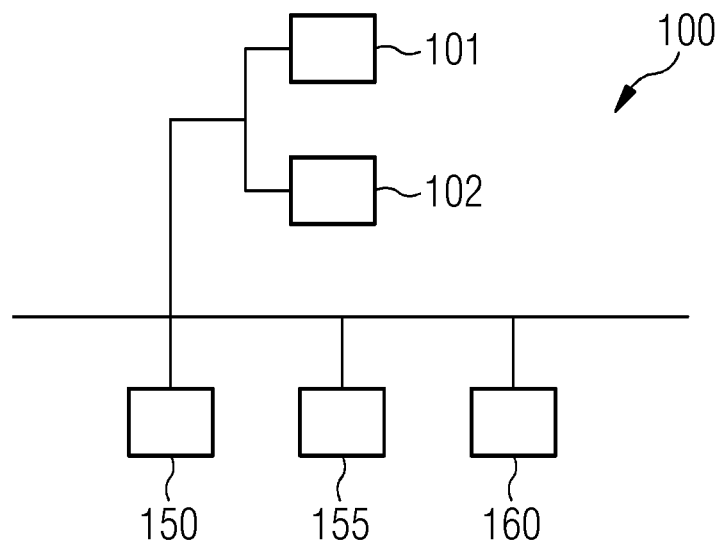
FIG. 1 is a schematic view of an x-ray device.

The present invention will be explained in more detail below on the basis of preferred embodiments and with reference to the drawings. In the drawings, the same reference signs denote equivalent or similar elements. The figures are schematic representations of various embodiments of the invention. Elements depicted in the figures are not necessarily depicted true to scale. Rather, the various elements depicted in the figures are reproduced in such a way that the function and general purpose thereof become clear to a person skilled in the art. Connections and couplings between functional units and elements depicted in the figures can also be interpreted as indirect connections or couplings. A connection or coupling can be implemented in a wired or wireless fashion. Functional units can be implemented as hardware, software or a combination of hardware and software.

Techniques in which a combined x-ray image is produced from a plurality of acquired x-ray images are described below. To this end, an x-ray tube of an x-ray device is adjusted by rotating and positioning between the acquisition of each x-ray image. Since a focal point of the x-ray tube is spaced apart from a point of rotation about which the rotation takes place, what the positioning achieves is that the position of the focal point does not change significantly from x-ray image to x-ray image.

FIG. 1 schematically depicts an x-ray device 100. The x-ray device 100 comprises an x-ray tube 101 which is configured to generate x-rays. Furthermore, the x-ray device 100 comprises an x-ray detector 102 which is configured to detect the x-rays. It is possible to arrange an examination object between the x-ray tube 101 and the x-ray detector 102 such that one or more x-ray images thereof can be acquired by means of the x-rays. The x-ray tube 101 and the x-ray detector 102 are adjustable separately from one another, i.e. they can be rotated and positioned. An orientation of the x-ray tube 101 together with the positioning thereof defines a pose of the x-ray tube 101. The pose determines a perspective of the corresponding x-ray image.

Furthermore, the x-ray device 100 comprises a control unit 150 configured to control various operating parameters of the x-ray device 100. By way of example, the control unit 150 can control the pose of the x-ray tube 101. In the x-ray device 100, position and orientation of the x-ray detector 102 can be adjusted separately from the pose of the x-ray tube 101. These operating parameters can also be controlled by the control unit 150.

Furthermore, the control unit 150 can initiate the acquisition of x-ray images. To this end, it is possible to set various parameters, such as e.g. exposure time, dose, etc.

By way of example, to this end, there can be an interaction with a user of the x-ray device 100 by way of a user interface 155. By way of example, the user interface 155 can comprise a screen, a mouse, a keyboard etc. Input and output of information from and to a user is possible thereby.

The x-ray device 100 furthermore comprises a computer unit 160 configured to produce a combined x-ray image from a plurality of acquired x-ray images. By way of example, this can be implemented by means of a simple superposition of the various acquired x-ray images. It would also be possible for the computer unit 160 to additionally be configured to carry out various image-processing steps on the acquired x-ray images. The combined x-ray image can then be output to the user of the x-ray device 100 by way of the user interface 155. As a result, subsequent diagnosis steps are possible.

Figure 2:
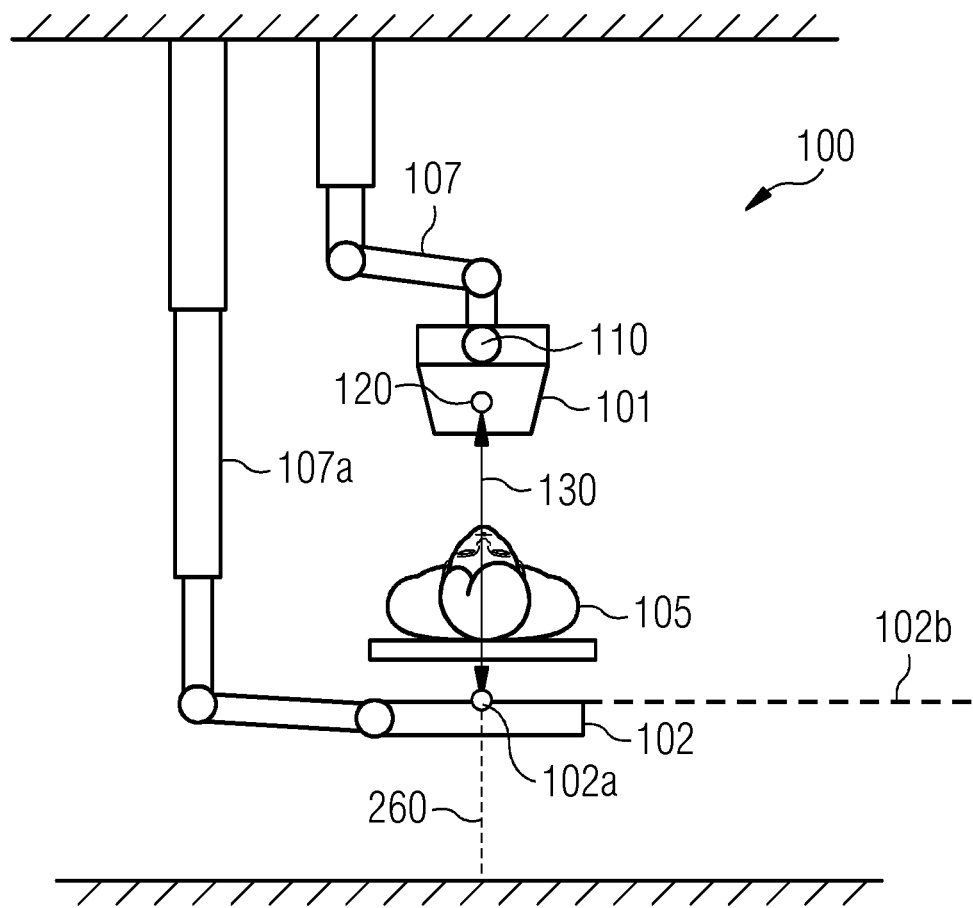
FIG. 2 shows an x-ray device, in which a point of rotation of an x-ray tube is spaced apart from a focal point of the x-ray tube.

FIG. 2 depicts mechanical details of the x-ray device 100. The x-ray tube 101 is fastened to the ceiling by way of a holder 107. The x-ray detector 102 is correspondingly fastened to the ceiling by way of a holder 107a. FIG. 2 furthermore plots the examination object 105, who/which is arranged between the x-ray tube 101 and the x-ray detector 102. The focal point 120, which is situated at an anode (not depicted in FIG. 2) of the x-ray tube 101, is the optically effective initial point of x-rays.

The position and orientation of the x-ray tube, relatively in relation to the examination object 105 or in relation to the x-ray detector 102 or a machine coordinate system, define a film/focus distance 130. The film/focus distance 130 connects the focal point 120 with the detector plane 102b, wherein the film/focus distance 130 is parallel to the central ray 260 (plotted using a dashed line in FIG. 2) of the x-rays. The central ray 260 is defined by way of a center of a beam path (not plotted in FIG. 2) or by way of a cross-sectional area of the beam path of the x-rays. In FIG. 2, the x-ray tube 101 and the x-ray detector 102 are arranged in such a way that the central ray 260 is placed substantially centrally, i.e. near the center point 102a of the x-ray detector 102, on the x-ray detector 102.

FIG. 2 furthermore plots a point of rotation 110 of the x-ray tube 101. The point of rotation 110 is spaced apart from the focal point 120 by a certain distance. If the x-ray tube 101 or the focal point 120 is oriented by way of rotation, this rotation is implemented about the point of rotation 110. Therefore, the position of the focal point 120 changes during the rotation. Hence, the pose with which an x-ray image is acquired changes. This can, in turn, lead to parallax errors when producing a combined x-ray image.

FIG. 3 depicts the acquisition of a first x-ray image 201 for the pose of the x-ray tube 101 as depicted in FIG. 2. A first solid angle 211, which is exposed when acquiring the first x-ray image 201, is depicted. The first solid angle 211 is defined by way of the beam path 270 of the x-rays. The cone beam geometry of the x-ray device 100 is illustrated in FIG. 3 by the broadening of the beam path 270: from FIG. 3, it is possible to see that the cross-sectional area of the beam path 270 of the x-rays increases along the central ray 260 for increasing distances from the focal point 120.

FIG. 4 depicts the acquisition of a second x-ray image 202. The focal point 120 is situated at the same position as in FIG. 3. However, while the focal point 120 in FIG. 3 was in a first orientation, the focal point 120 in FIG. 4 is in a second orientation: in particular, a second solid angle 212 is exposed when acquiring the second x-ray image 202 and the central ray 260 of FIG. 4 is rotated by a predetermined angle in relation to the central ray 260 in FIG. 3.

It is clear from a comparison between FIG. 3 and FIG. 4 that the x-ray tube 101 was adjusted. In particular, the x-ray tube 101 or the focal point 120 was rotated about the predetermined angle about the point of rotation 110. In order to obtain the focal point 120 being situated at respectively the same predetermined position when acquiring the first and second x-ray image 201, 202, there furthermore is positioning of the focal point 120 within the scope of the adjustment. The positioning has a longitudinal component 302 and a transverse component 301.

What is furthermore clear from a comparison between FIG. 3 and FIG. 4 is that the adjustment furthermore comprises an adjustment of the x-ray detector 102 by rotation and positioning. The detector plane 102b of the x-ray detector 102 is perpendicular to the central ray 260 when respectively acquiring the first and the second x-ray image 201, 202. Moreover, the film/focus distance 130 is the same in each case. The central ray 260 also lies substantially centrally on the x-ray detector 102 in both cases.

In a case as depicted in FIGS. 3 and 4, the production of the combined x-ray image 205 (cf. FIG. 5) can comprise the superposition of the first and second x-ray image 201, 202. As can be seen from FIG. 5, this superposition has a specific overlap 280 (depicted in a dashed manner in FIG. 5) in the case of FIGS. 3 and 4.

Figure 5:
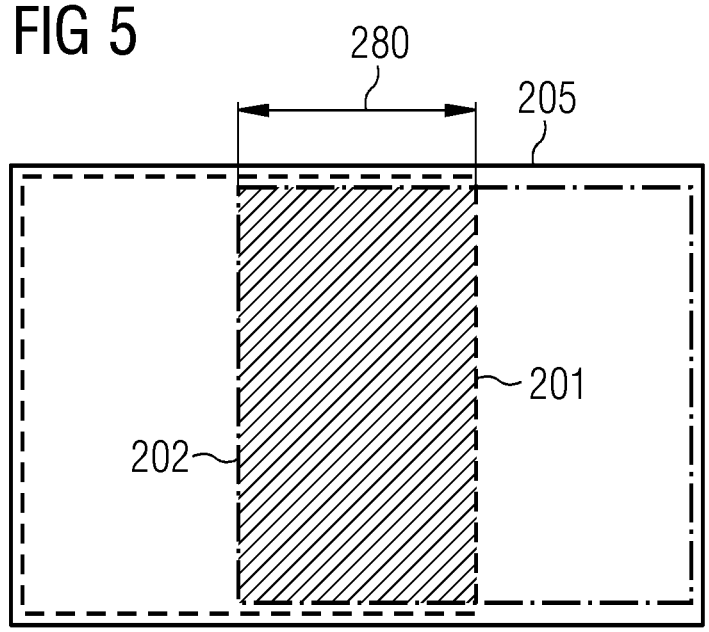
FIG. 5 shows the production of a combined x-ray image from the first and second x-ray image from FIGS. 3 and 4, wherein there is a certain amount of overlap between the first and the second x-ray image.
Figure 6:
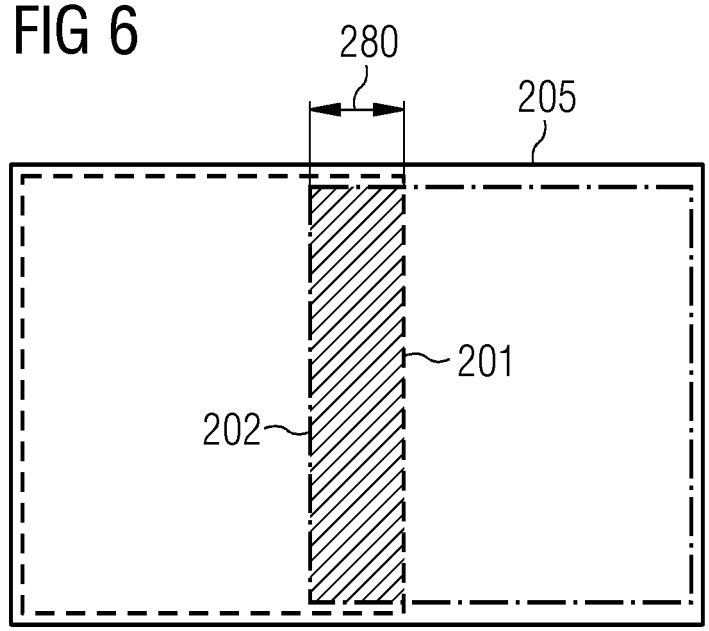
FIG. 6 shows the scenario of FIG. 5, in which there is a smaller overlap.
Figure 7:
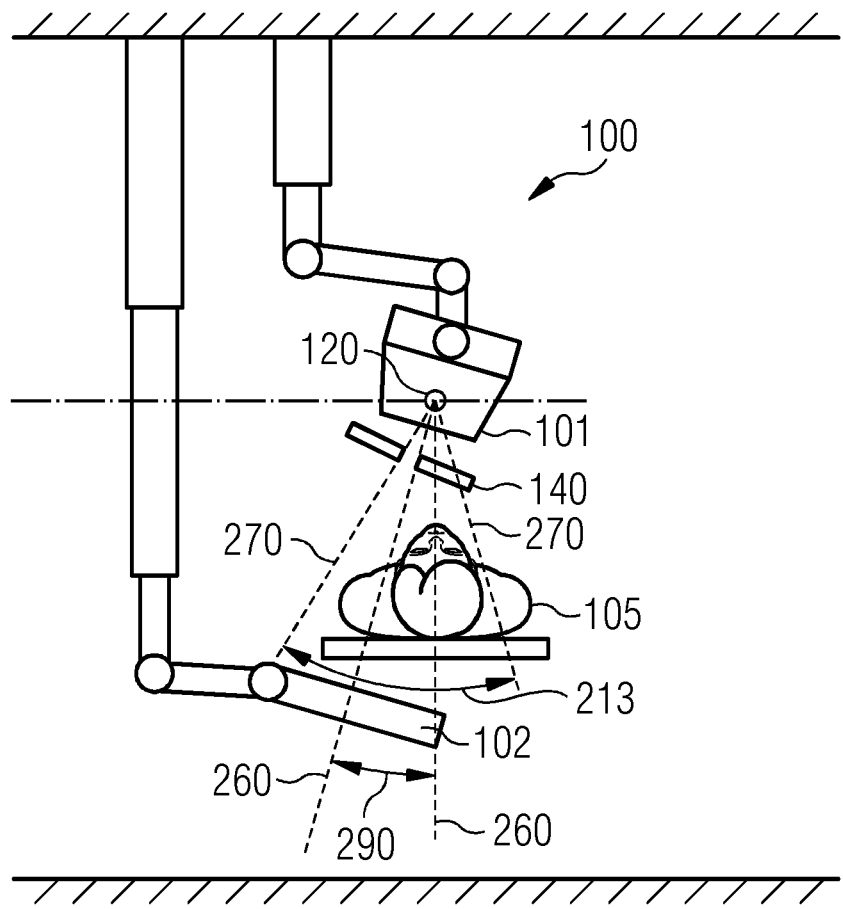
FIG. 7 shows the scenario of FIG. 4, wherein an x-ray stop is arranged in a beam path of the x-rays.

FIG. 6 depicts a situation in which the overlap 280 assumes a smaller value than in FIG. 5. In particular, it may be desirable for the overlap 280 to assume a predetermined value. To this end, it may be possible to arrange an x-ray stop 140 (cf. FIG. 7) in the beam path of the x-rays. In the case of FIG. 7, the x-ray stop 140 is arranged in the beam path 270 of the x-rays in such a way that the overlap 280 equals zero.

FIG. 7 furthermore plots a solid angle region 213 which can be obtained from a user of the x-ray device 100, for example by means of the user interface 155. The whole solid angle region 213 is imaged by acquiring the first and second x-ray image 201, 202. The combined x-ray image 205 images the solid angle region 213. By way of example, it is possible that the user of the x-ray device 100 merely specifies the solid angle region 213 and that the predetermined angle 290, by means of which the focal point 120 is rotated within the scope of orienting, is determined as a function of the solid angle region 213. What is illustrated in FIG. 7 is that the predetermined angle 290 is defined in respect of the rotation of the central ray 260.

What can furthermore be seen from FIG. 7 is that, when the x-ray stop 140 is used, the central ray 260 need not necessarily lie in the center of the beam path 270 of the x-rays downstream of the x-ray stop 140.

FIG. 8 depicts a flowchart of a method for imaging by means of the x-ray device 100 in accordance with various aspects of the present invention. The method starts with step X1. Initially, there is the acquisition of the first x-ray image 201 at the predetermined position of the focal point 120 or the x-ray tube 101 and with the first orientation of the focal point 120 or the x-ray tube 101 (step X2).

Subsequently the x-ray tube 101 and, optionally, the x-ray detector 102 are adjusted in step X3. The adjustment comprises the positioning and orienting of the x-ray tube 101 such that the pose of the x-ray tube 101 changes. In particular, the x-ray tube 101 is rotated by the predetermined angle 290 within the scope of step X3. Moreover, the x-ray tube 101 is positioned within the scope of step X3 in such a way that the position of the focal point 120 is the same before and after step X3. In particular, the position of the focal point 120 can be the same in relation to the examination object 105.

Then, the second x-ray image is acquired in step X4 at the predetermined position and with the second orientation of the focal point 120.

The combined x-ray image 205 is produced in step X5, in particular by superposing the first and the second x-ray image 201, 202. In this manner, the combined x-ray image 205 can be produced with only small, or no, parallax errors. In particular, the production of the combined x-ray image 205 can be carried out comparatively quickly. The measurement duration is short.

The method ends in step X6.

FIG. 9 depicts geometric relationships for rotating the focal point 120 when acquiring the first x-ray image 201 and the second x-ray image 202. In particular, the distance 115 is depicted between the point of rotation 110 and the focal point 120. The positioning of the focal point 120 within the scope of the adjustment is carried out in such a way that the focal point 120 is situated at the same position when acquiring the first and second x-ray image 201, 202. In FIG. 9, this positioning is depicted by a dashed arrow. In particular, the positioning can be decomposed into the longitudinal and transverse components 301, 302.

Naturally, the features of the aspects of the invention and embodiments described above can be combined with one another. In particular, the features can be used not only in the described combinations, but also in other combinations or on their own, without departing from the field of the invention.

LIST OF REFERENCE SIGNS

100 X-ray device
101 X-ray tube
102 X-ray detector
102a Center point of the x-ray detector
102b Detector plane
105 Person under examination
107 Holder
107a Holder
110 Point of rotation
115 Distance
120 Focal point
130 Film/focus distance
140 X-ray stop
150 Control unit
155 User interface
160 Computer unit
201 First x-ray image
202 Second x-ray image
205 Combined x-ray image
211 First solid angle
212 Second solid angle
213 Combined solid angle
260 Central ray
270 Beam path
280 Overlap
290 Angle
301 Transverse adjustment
302 Longitudinal adjustment
X1-X8 Step

The invention claimed is:

1. A method for imaging, which comprises the following steps of:
providing an x-ray device having an x-ray detector and an x-ray tube with a focal point being adjustable by positioning the x-ray tube;
acquiring a first x-ray image at a predetermined position of the focal point and with a first orientation of the x-ray tube;
adjusting the x-ray tube by a rotation about a predetermined angle at a point of rotation being spaced apart from the focal point by a distance and by positioning the focal point, wherein the focal point is at the predetermined position prior to performing the step of adjusting the x-ray tube and after performing the step of adjusting the x-ray tube, wherein the x-ray tube has a second orientation after the adjustment, wherein a positioning of the focal point contains at least one of a longitudinal component or a transverse component, wherein at least one of the longitudinal component or the transverse component is determined on a basis of the distance between the point of rotation and the focal point and on a basis of the predetermined angle;

acquiring a second x-ray image at the predetermined position of the focal point and with the second orientation of the x-ray tube; and producing a combined x-ray image from at least the first x-ray image and the second x-ray image by superposing the first x-ray image and the second x-ray image.

2. The method according to claim 1, wherein the x-ray detector is adjustable in a manner decoupled from the x-ray tube;

wherein the adjustment includes the adjustment of the x-ray detector by rotating and positioning the x-ray detector;

wherein, prior to the adjustment and after the adjustment:
a detector plane of the x-ray detector lies perpendicular to a central ray of x-rays in each case; and/or
a film/focus distance between the focal point and the detector plane is the same in each case; and/or
the central ray is placed substantially centrally on the x-ray detector.

3. The method according to claim 1, which further comprises disposing an x-ray stop in a beam path of x-rays such that a first solid angle exposed when acquiring the first x-ray image and a second solid angle exposed when acquiring the second x-ray image have a predetermined overlap.

4. The method according to claim 1, which further comprises:
obtaining a solid angle region which is intended to be imaged by the combined x-ray image by means of a user interface; and
calculating the predetermined angle in dependence on the solid angle region obtained.

5. An x-ray device, comprising;
an x-ray detector;
an x-ray tube, said x-ray tube having a focal point and a position of the focal point being adjustable by positioning said x-ray tube, an orientation of said x-ray tube being adjustable by rotating said x-ray tube about a point of rotation, and the point of rotation being spaced apart from the focal point by a distance;
a control unit configured to:
acquire a first x-ray image at a predetermined position of the focal point and with a first orientation of said x-ray tube;
adjust said x-ray tube by rotating about a predetermined angle at the point of rotation and by positioning of the focal point, the focal point being at the predetermined position prior to the adjustment and after the adjustment, and said x-ray tube has a second orientation after the adjustment;
acquire a second x-ray image at the predetermined position of the focal point and with the second orientation of said x-ray tube;

said x-ray device having a computing unit configured to produce a combined x-ray image from at least the first x-ray image and the second x-ray image by superposing the first x-ray image and the second x-ray image; and the positioning of the focal point contains at least one of a longitudinal component or a transverse component, at least one of the longitudinal component or the transverse component is determined on a basis of the distance between the point of rotation and the focal point and on a basis of the predetermined angle.

6. The x-ray device according to claim 5, wherein:

said x-ray detector is adjustable in a manner decoupled from said x-ray tube;

said control unit is configured such that the adjustment contains the adjustment of said x-ray detector by rotating and positioning said x-ray detector;

prior to the adjustment and after the adjustment, a detector plane of said x-ray detector lies perpendicular to a central ray of x-rays in each case; and/or
a film/focus distance between the focal point and the detector plane is the same in each case; and/or
the central ray is placed substantially centrally on the x-ray detector.

7. The x-ray device according to claim 5, wherein:

the x-ray device has an x-ray stop; and said control unit is configured to dispose said x-ray stop in a beam path of the x-rays in such a way that a first solid angle exposed when acquiring the first x-ray image and a second solid angle exposed when acquiring the second x-ray image have a predetermined overlap.

* * * * *